United States Patent [19]

Yoshimoto et al.

[11] 4,234,678
[45] Nov. 18, 1980

[54] LIGHT-SENSITIVE SILVER HALIDE PHOTOGRAPHIC MATERIALS

[75] Inventors: Shinji Yoshimoto, Hachioji; Mitsuto Fujiwhara, Tokyo; Shoji Kikuchi, Hachioji; Ryosuke Satoh, Koganei; Takaya Endo; Satoshi Nakagawa, both of Hino, all of Japan

[73] Assignee: Konishiroku Photo Industry Co., Ltd., Tokyo, Japan

[21] Appl. No.: 962,793

[22] Filed: Nov. 20, 1978

[30] Foreign Application Priority Data

Nov. 23, 1977 [JP] Japan .................................. 52-140927

[51] Int. Cl.³ ............................................. G03C 1/06
[52] U.S. Cl. .................................... 430/564; 430/382; 430/445; 430/446; 430/448; 430/544; 430/957
[58] Field of Search ........................... 96/95, 66.3

[56] References Cited

U.S. PATENT DOCUMENTS

| | | | |
|---|---|---|---|
| 3,958,993 | 5/1976 | Fujiwhara et al. | 96/95 |
| 3,961,959 | 6/1976 | Fujiwhara et al. | 96/95 |
| 4,010,035 | 3/1977 | Fukiwhara et al. | 96/66.3 |
| 4,063,950 | 12/1977 | Fujiwhara et al. | 96/66.3 |
| 4,153,460 | 5/1979 | Iijima et al. | 96/74 |

*Primary Examiner*—Travis Brown
*Attorney, Agent, or Firm*—Haseltine, Lake & Waters

[57] ABSTRACT

A photographic material having a light-sensitive silver halide emulsion layer coated on a support and containing a compound, useful as a development inhibitor of the formula:

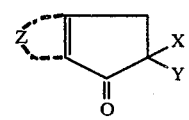

wherein X, Y and Z are as herein defined, is described.

7 Claims, No Drawings

LIGHT-SENSITIVE SILVER HALIDE PHOTOGRAPHIC MATERIALS

This invention relates to light-sensitive silver halide photographic materials containing a novel development inhibitor releasing substance (hereinafter called "DIR substance") which releases a development inhibitor on reaction with an oxidation product of a developing agent. It has heretofore been well known that a compound capable of releasing at the time of development a development inhibitor correspondingly to a density of the resulting image is previously incorporated into light-sensitive silver halide photographic materials. This compound is a compound of the type which generally reacts with an oxidation product of a color developing agent to release a development inhibitor, and the so-called DIR couplers having introduced into the active point of coupler a group which will come to have a development inhibiting action when it is released from said active point are known as representatives of the compound of the type.

The DIR coupler has such properties that when it has undergone coupling reaction with an oxidation product of a color development agent, the coupler residue forms a dye, on the other hand, releases a development inhibitor. The known DIR couplers of the type are such compounds as disclosed in British Patent Specification No. 935,454, U.S. Pat. Nos. 3,337,554, 3,701,783, 3,615,506 and 3,617,291. The DIR couplers of the type mentioned above have both an inter-image effect that color reproductivity can be enhanced by masking action wherein a development inhibitor is released at the time of color development correspondingly to a density of dye image formed in a silver halide emulsion layer through which the development inhibitor diffuses and thereby to inhibit development of a silver halide emulsion layer into which said development inhibitor diffuses, and the so-called intra-image effect that the inhibition of development correspondingly to the dye image density results in a significant contribution to an effective control of image tone, obtainment of fine grain image and improvement on image in sharpness. Because the DIR coupler contributes to color reproduction by forming a dye at the time of color development, however, an absorption wavelength of the dye to be formed should be taken into account when said DIR coupler is actually used, and hence it becomes very difficult to find compounds suitable for use as the coupler of the type. On that account, these DIR couplers are generally associated with such drawbacks that when a coupler advantageously suitable for color reproduction is selected, the coupler selected is found to fail to show sufficient inhibition effect and, on the other hand, when a coupler having sufficient inhibition effect is selected, the coupler selected is then found to be insufficient in color reproductivity or to cause desensitization effect. Differently from the above-mentioned DIR couplers, furthermore, there have been known such compound which, when reacted with an oxidation product of a color developing agent at the time of color development, releases a development inhibitor simultaneously with a colorless compound as disclosed in U.S. Pat. Nos. 3,632,345 and 3,958,993 and Japanese Laid-Open-to-Public Publication No. 64927/1976. These compounds are technically known as DIR substances in distinction from the so-called DIR couplers. The DIR substances have such preferable advantages that because of a reaction product with an oxidation product of a color developing agent being colorless, they can be used in any silver halide emulsion layers, either blue-sensitive green-sensitive or red-sensitive, and that as compared with the case of the DIR coupler which forms a dye, a relatively wide free-command of selection of the parent body of coupler is possible. The prior art DIR substances mentioned above, however, include those which are poor in reactivity with an oxidation product of a color developing agent. On that account, no sufficient inhibition effect can be attained unless large amounts of the prior art DIR substances are used, and this results in such drawbacks that an undesirable influence comes to exert on photographic characteristics, such as fall in sensitivity, formation of stain, degradation of emulsions in storability and so forth. Accordingly, an object of the present invention is to provide light-sensitive silver halide photographic materials containing DIR substances which are high in reactivity with an oxidation product of a color developing agent, have a sufficiently high inhibition effect even when used in small amounts and which are sharply high in storability when stored in any emulsions as compared with the prior art DIR substances.

The above-mentioned object of the present invention can be accomplished by incorporating a novel DIR substance represented by the following general formula [I] into a light-sensitive silver halide photographic material.

General formula [I]

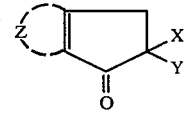

In the above general formula, X represents hydrogen or halogen atom (chlorine, bromine or the like atoms).

On the other hand, the Y substituent is a group which releases on reaction with an oxidation product of a color developing agent, thereby to form an arylmercapto compound, a heterocyclic mercapto compound or a triazole compound which has no mercapto group, each having a development inhibition action.

The heterocyclic mercapto compound includes a mercapto group having 5- to 7-membered heterocyclic ring containing a nitrogen, oxygen and/or sulfur atom, for example, mercaptotetrazole compounds (e.g. 1-phenyl-5-mercaptotetrazole, 1-nitrophenyl-5-mercaptotetrazole, 1-naphthyl-5-mercaptotetrazole, etc.), mercaptothiazole compounds (e.g. 2-mercaptobenzthiazole, 2-mercaptonaphthothiazole, etc.), mercaptooxadiazole compounds (e.g. 5-mercapto-1,2,4-oxadiazole, etc.), mercaptopyrimidine compounds (e.g. 4-mercaptopyrimidine, etc.), mercaptothiadiazole compounds (e.g. 2-mercapto-1,3,4-thiadiazole, etc.), mercaptotriazine compounds (e.g. 2-mercapto-1,3,5-triazine, etc.) and mercaptotriazole compounds (e.g. 3-mercapto-1,2,4-triazole, etc.).

The arylmercapto compound includes mercaptobenzene compounds (e.g. 1-mercapto-2-benzoic acid, 1-mercapto-3-nitrobenzene, 1-mercapto-3-heptadecanoylaminobenzene, etc.).

The triazole compound includes, as useful compounds, benzotriazole compounds in which the triazole has attached to the 1- or 2-position of the benzene ring (e.g. 5-methylbenzotriazole, 5-bromobenzotriazole, 5- octadecaneamidobenzotriazole, 5-benzyloxybenzotriazole, etc.). Z represents a nonmetal atomic group necessary for forming a benzene ring, said benzene ring having been substituted by at least one —S—R group and/or a group having at least one —S—R group, namely the general formula [I] may be rewritten by the following formulae [I-a] and [I-b]:

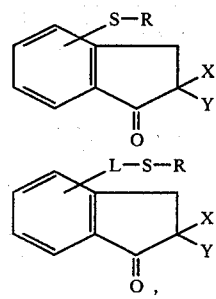

wherein L represents a connecting group, and X, Y and R are the same meaning as defined in the formula [I].

R represents an alkyl, aryl or heterocyclic group, each may have a substituent. The alkyl group more particularly includes saturated or unsaturated, straight chain or branched alkyl groups of up to 22, preferably 12 to 18, carbon atoms, or 5- to 7-membered cycloalkyl groups. These alkyl groups may have at least one substituent such as halogen, hydroxyl, alkoxy, aryloxy, aryl, 5- or 6-membered heterocyclic containing a nitrogen, oxygen or hydrogen atom or the like groups. The aryl group represented by R is preferably a phenyl or naphthyl group, and these aryl groups may have at least one substituent such as a lower alkyl group, halogen atom, an acylamino, alkylamino, alkoxy, aryloxy, alkoxycarbonyl, sulfamoyl, carbamoyl, nitro, cyano or the like groups. Further, the heterocyclic group represented by R is preferably a 5- or 6-membered heterocyclic ring containing, as heteroatoms, nitrogen, oxygen, sulfur or the like atoms, and a condensed heterocyclic group, for example, benzthiazole, oxadiazole, thiadiazole, triazine, triazole, diazole, pyrimidine, naphthothiazole and the like. These heterocyclic groups may have at least one substituent such as an alkyl group, halogen, an acylamino, alkylamino, alkoxy, aryloxy, alkoxycarbonyl, sulfamoyl, carbamoyl, nitro, cyano or the like group.

The compounds of the present invention are characterized in that a group having at least one —S—R group and/or at least one —S—R group has been introduced into a benzene ring represented by Z, namely, at least one —S—R group has been introduced either directly or through a connecting group into said benzene ring. In accordance with the present invention, there can be provided, by virtue of having the above-mentioned —S—R group on the benzene ring, the DIR substances which have sufficient inhibition effect even when used in small amounts and which are extremely high in storability when used with any emulsions, as compared with the prior art DIR substances. Accordingly, the connecting group for introducing the —S—R group into the benzene ring is not particularly limited but is selected from various organic groups. The DIR compounds of the present invention, the connecting group L is preferably an alkylene group of up to 22 (more preferably 12 to 22) carbon atoms, arylene group (e.g. phenylene, naphthylene, etc.), 5- or 6-membered heterocyclic residue containing a nitrogen or oxygen atom, acyl group residue and a composite divalent group having any combination of these groups as referred to above.

The heterocyclic residue mentioned above includes such groups as forming a succinic imide ring, a maleic imide ring, a hydantoin ring a pyrrolidone ring, a pirrolidine ring, a pyrazolidine ring, etc. Further, the aforesaid alkylene, arylene and heterocyclic residue may be substituted by such groups as referred to above as the substituents for the aforesaid alkyl, aryl and heterocyclic groups represented by R and may further be substituted, besides said substituents, by the —S—R group (R has the same meaning as defined in the aforementioned general formula).

In the aforesaid benzene ring, furthermore, at least one of various substituents may be present, besides the —S—R group and/or group having the —S—R group, such as an alkyl group, halogen, a hydroxyl, alkoxy, aryloxy or the like group.

In this connection, the present inventors, prior to accomplishment of the present invention, studied and investigated on the DIR substances comprising a DIR substance having X and Y as defined in the general formula of the present invention and having as a substituent the aforesaid —S—R group or group having the —S—R group at the α-position of a cyclic ketone such as cyclopentanone, cyclohexanone, tetralone, oxyindole, piperidone or the like. They did not see, however, any marked effects in the form of improvement in storability in these DIR substances as compared with the DIR compounds of the present invention.

Typical examples of the compound of the present invention are exemplified below, but it should be construed that the present compounds are not limited only to those as exemplified.

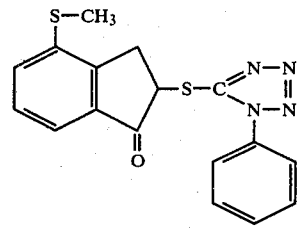

(1)

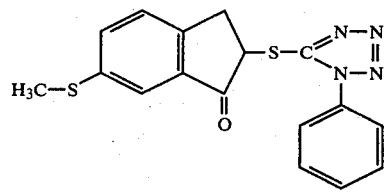

(2)

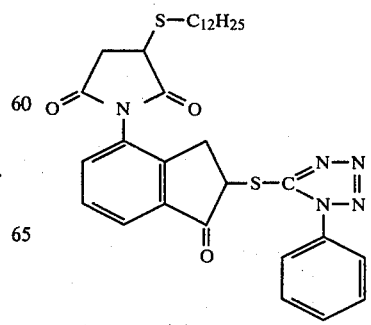

(3)

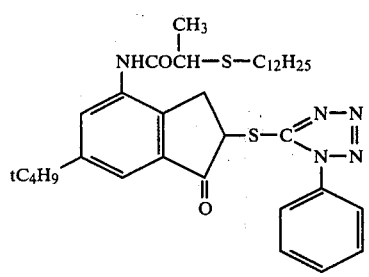

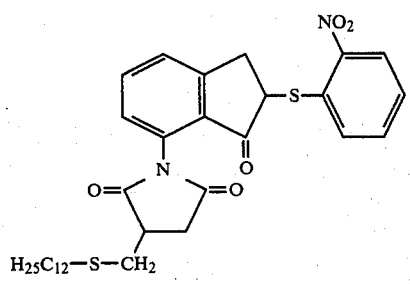
(16)
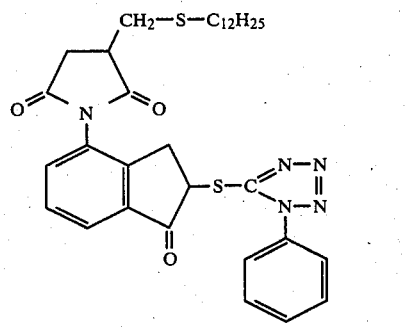
(17)
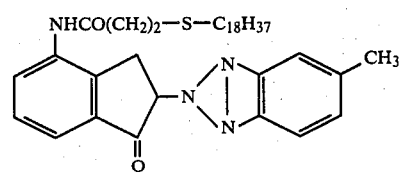
(18)
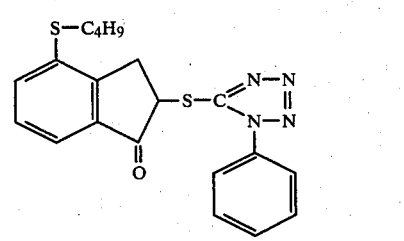
(19)
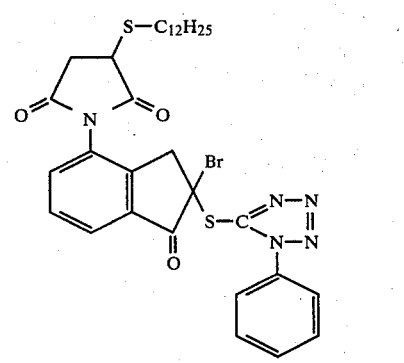
(20)
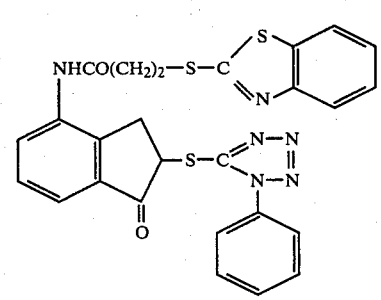
(21)
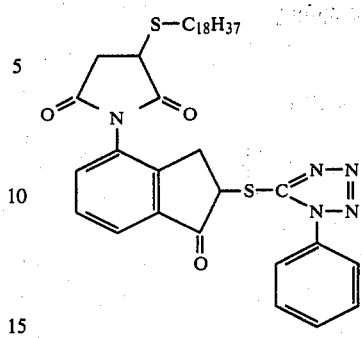
(22)
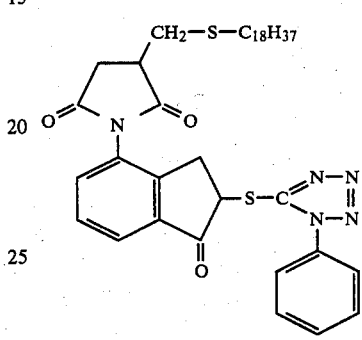
(23)
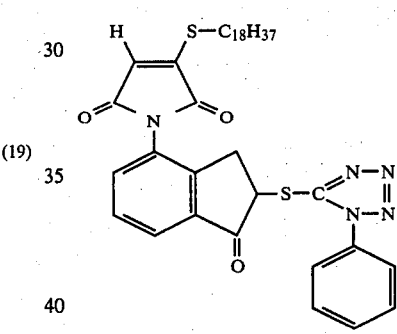
(24)
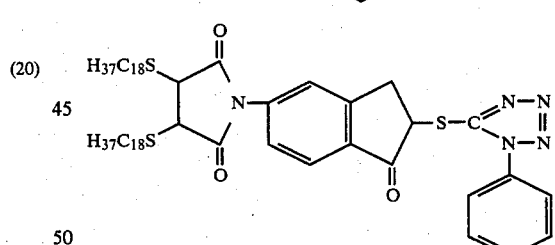
(25)
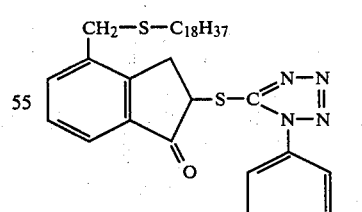
(26)
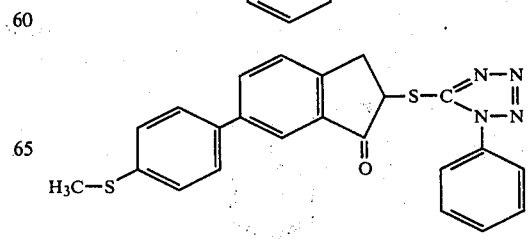
(27)

-continued

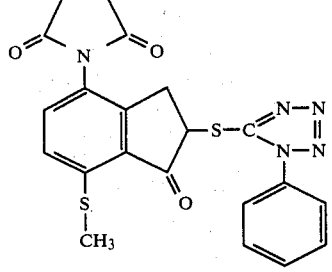
(28)

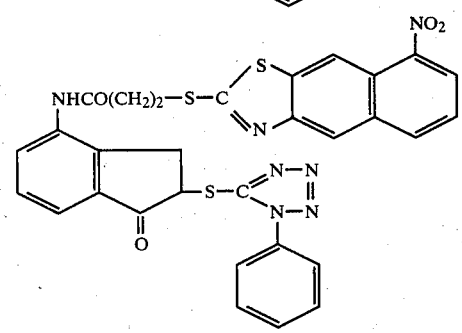
(29)

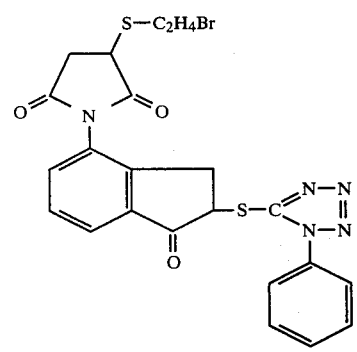
(30)

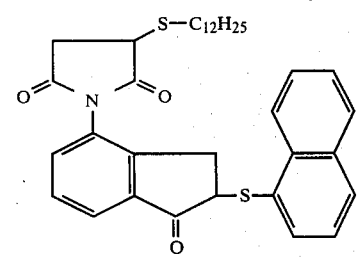
(31)

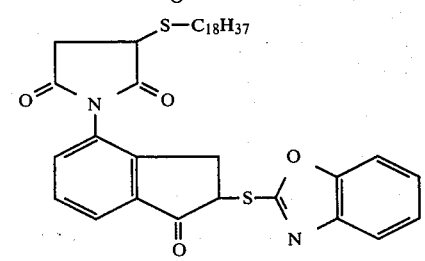
(32)

Typical processes for the synthesis of some of the above-exemplified compounds are illustrated below with reference to synthesis examples. It is needless to say that the remainder compounds are of course readily synthesized according to these processes are illustrated.

SYNTHESIS EXAMPLE 1

Preparation of exemplified compound (1)

(a) Synthesis of 4-Methylthio-1-indanone

To a solution of 50 g of o-methylthiocinnamic acid in 500 ml of carbon disulfide was gradually added with stirring 34 g of aluminum chloride, and the resulting mixture was then boiled with stirring for 3 hours. The reaction liquid after reaction was poured into a cooled 1 N aqueous hydrochloric acid solution and extracted with ethyl acetate. The ethyl acetate solution was washed with an aqueous potassium carbonate solution, followed by water-washing and then drying over anhydrous sodium sulfate, to remove the solvent therefrom. The residue was purified by column chromatography to obtain 18 g of the title compound.

(b) Preparation of exemplified compound (1)

Into a solution of 10 g of 4-methylthio-1-indanone in 100 ml of chloroform was dropped 10 g of bromine while maintaining the liquid temperature at 5° C. to 10° C. Thereafter, the liquid was allowed to undergo reaction at that temperature for 1 hour, and the reaction liquid was poured into water and the resulting chloroform layer was thoroughly washed with water. After having dried this chloroform layer, the solvent was distilled off and the residue was dissolved in 200 ml of acetone. The resulting solution was incorporated with 11.2 g of sodium salt of 1-phenyl-5-mercaptotetrazole and was boiled with stirring for 1 hour. Thereafter, the acetone was distilled off, and the residue incorporated with water was extracted with ethyl acetate and the ethyl acetate solution was thoroughly washed with water and dried over anhydrous sodium sulfate. After having distilled off the ethyl acetate, the residue was purified by column chromatography to obtain 9.7 g of the end product. The structure of this end product was confirmed by elementary analysis as well as by nuclear magnetic reasonance spectrum thereof.

SYNTHESIS EXAMPLE 2

Preparation of exemplified compound (3)

(a) Synthesis of 4-dodecylthiosuccinimido-1-indanone

A solution of 10 g of 4-amino-1-indanone and 20 g of anhydride of dodecylthiosuccinic acid in 200 ml of ethyl acetate was boiled with stirring for 1 hour. Subsequently, the ethyl acetate was distilled off and the residue incorporated with 200 ml of acetic anhydride was boiled with stirring for 1 hour. After reaction, the acetic anhydride was distilled off. The resultant residue was recrystallized from 100 ml of petroleum ether using 5 g of active carbon to obtain 23 g of the title compound.

(b) Preparation of exemplified compound (3)

Into a solution of 20 g of 4-dodecylthiosuccinimido-1-indanone in 200 ml of chloroform was gradually dropped 8.2 g of bromine while maintaining the liquid temperature at 10° C. to 15° C. After completion of the dropping, the reaction was continued at 10° C. to 15° C. for about 1 hour. After the reaction was over, the reaction liquid was washed with water and dried, and the chloroform was distilled off and the residue was dissolved in 200 ml of acetone. The resulting solution was incorporated with 9.3 g of sodium salt of 1-phenyl-5-mercaptotetrazole and boiled with stirring for 30 minutes. Thereafter, the acetone was distilled off and the residue incorporated with water was extracted with ethyl acetate, followed by thorough water washing, and the ethyl acetate solution was dried over anhydrous sodium sulfate. After having distilled off the ethyl acetate, the residue was purified by column chromatography to obtain 12.4 g of the end product. The structure of this end product was confirmed by elementary analysis as well as nuclear magnetic resonance spectrum thereof.

SYNTHESIS EXAMPLE 3

Preparation of exemplified compound (20)

50 Grams of 2-(1-phenyl-5-tetrazolylthio)-4-dodecylthiosuccinimido-1-indanone synthesized according to the procedure of Synthesis Example 2 was dissolved in 500 ml of chloroform and thereinto was dropped 14.5 g of bromine while maintaining the liquid temperature at 20° C. to 25° C. After completion of the dropping, the reaction was continued for 20 minutes and the reaction liquid was washed with water, rinsed with a 5% aqueous sodium bicarbonate solution, washed with water and dried over anhydrous sodium sulfate. Thereafter, the chloroform was distilled off and the residual product in a syrup-like form was purified by column chromatography to obtain 22 g of the end product. The structure of this end product was confirmed by elementary analysis as well as nuclear magnetic resonance spectrum thereof.

SYNTHESIS EXAMPLE 4

Preparation of exemplified compound (10)

(a) Synthesis of 4-(β-octadecylthiopropaneamido)-1-indanone

Into a solution of 10 g of 4-amino-1-indanone and 10 ml of N,N-dimethylaniline in 100 ml of acetonitrile was dropped with stirring 28 g of β-octadecylthiopropionic acid chloride while maintaining the liquid temperature at 10° C. to 15° C. After the dropping, the resulting mixture was stirred at room temperature for 1 hour. After the reaction was over, the reaction liquid was filtered with suction to remove precipitates therefrom and the liquid was poured into 1000 ml of water. After having been separated by filtration and dried, the deposited solids were recrystallized from ethanol to obtain 13 g of the title compound.

(b) Preparation of exemplified compound (10)

Into a solution of 20 g of 4-(β-octadecylthiopropaneamido)-1-indanone in 200 ml of chloroform was dropped 7.2 g of bromine while maintaining the liquid temperature at 0° C. to 5° C. After completion of the dropping, the resulting mixture was stirred for 1 hour. After the reaction was over, the reaction liquid was washed with water and dried over anhydrous sodium sulfate, and the solvent was then distilled off to obtain a solid in a syrup-like form. This solid was dissolved in 100 ml of acetonitrile and then incorporated with 4.3 g of potassium salt of 2-bromobenzotriazole, and the resulting mixture was boiled with stirring for 2 hours. After the reaction was over, the solvent was distilled off from the reaction liquid and the residue was extracted with ether, followed by water washing and drying over anhydrous sodium sulfate, and then the ether was distilled off and the residue was purified by column chromatography to obtain 9.8 g of the end product. The structure of this end product was confirmed by elementary analysis as well as nuclear magnetic resonance spectrum thereof.

SYNTHESIS EXAMPLE 5

Preparation of Exemplified compound (18)

10 Grams of 4-(β-octadecylthiopropaneamido)-2-(2-nitro-4-methylphenylazo)-1-indanone obtained by reacting 4-(β-octadecylthiopropaneamido)-1-indanone synthesized according to the procedure of (a) of Synthesis Example 4 with 2-nitro-4-methylbenzenediazonium chloride was dissolved in 300 ml of a mixture comprising ethanol and a 30% aqueous hydroxide solution, and the resulting solution was incorporated with zinc powder and boiled under reflux. After the reaction was over, the reaction mixture was filtered and the filtrate was poured into water, followed by acidification with hydrochloric acid. The reaction liquid thus treated was extracted with ethyl acetate and dried over anhydrous sodium sulfate, and then the ethyl acetate was distilled off. The resulting oily product was purified by column chromatography to obtain 4.8 g of the end product. The structure of this end product was confirmed by elementary analysis as well as nuclear magnetic resonance spectrum thereof.

The exemplified compounds prepared in the manner as above had their respective analysis values for S as shown in the following table.

TABLE

| Exemplified compound | Molecular formula | Elementary analysis value (S) Calculated | Found |
|---|---|---|---|
| (1) | $C_{17}H_{14}N_4OS_2$ | 18.09 | 18.03 |
| (2) | $C_{17}H_{14}N_4OS_2$ | 18.09 | 17.87 |
| (3) | $C_{32}H_{39}N_5O_3S_2$ | 10.58 | 10.23 |
| (4) | $C_{35}H_{49}N_5O_2S_2$ | 10.08 | 10.36 |
| (5) | $C_{32}H_{42}N_2O_3S_3$ | 16.06 | 15.94 |
| (6) | $C_{39}H_{48}ClN_5O_5S_2$ | 8.36 | 8.22 |
| (7) | $C_{37}H_{45}ClN_4O_4S$ | 4.73 | 4.68 |
| (8) | $C_{32}H_{38}BrN_5O_3S_2$ | 9.36 | 9.40 |
| (9) | $C_{38}H_{55}N_5O_3S_2$ | 9.24 | 9.20 |
| (10) | $C_{36}H_{51}BrN_4O_2S$ | 4.69 | 4.73 |
| (11) | $C_{38}H_{43}N_5O_3S_2$ | 9.40 | 9.30 |
| (12) | $C_{37}H_{52}ClN_5O_2S_2$ | 9.18 | 9.10 |
| (13) | $C_{37}H_{41}BrN_4O_3S$ | 4.57 | 4.56 |
| (14) | $C_{33}H_{39}ClN_2O_3S_3$ | 14.95 | 15.00 |
| (15) | $C_{32}H_{39}ClN_4O_3S$ | 5.39 | 5.34 |
| (16) | $C_{32}H_{40}N_2O_5S_2$ | 10.74 | 10.28 |
| (17) | $C_{33}H_{41}N_5O_3S_2$ | 10.34 | 10.33 |
| (18) | $C_{37}H_{54}N_4O_2S$ | 5.18 | 5.31 |
| (19) | $C_{20}H_{20}N_4OS_2$ | 16.17 | 16.04 |
| (20) | $C_{32}H_{38}BrN_5O_3S_2$ | 9.36 | 9.25 |
| (21) | $C_{26}H_{20}N_6O_2S_3$ | 17.66 | 17.60 |
| (22) | $C_{38}H_{51}N_5O_3S_2$ | 9.29 | 9.33 |
| (23) | $C_{39}H_{53}N_5O_3S_2$ | 9.10 | 9.16 |
| (24) | $C_{38}H_{49}N_5O_3S_2$ | 9.32 | 9.28 |
| (25) | $C_{56}H_{87}N_5O_3S_2$ | 9.87 | 9.65 |
| (26) | $C_{35}H_{50}N_4OS_2$ | 10.56 | 10.22 |
| (27) | $C_{23}H_{18}N_4OS_2$ | 14.89 | 14.66 |
| (28) | $C_{39}H_{53}N_5O_3S_3$ | 13.06 | 12.88 |
| (29) | $C_{26}H_{19}N_7O_4S_3$ | 16.31 | 16.48 |
| (30) | $C_{22}H_{18}BrN_5O_3S_2$ | 11.78 | 11.82 |
| (31) | $C_{35}H_{41}NO_3S_2$ | 10.90 | 10.82 |
| (32) | $C_{38}H_{50}N_2O_4S_2$ | 9.67 | 9.71 |

The compounds of the present invention as prepared in the manner explained above are advantageously usable in various types of light-sensitive silver halide photographic materials, for example, those for use in black-and-white, color or pseudocolor photography, and also applicable to light-sensitive silver halide photographic materials for such purposes as ordinary black-and-white for photoprinting, X-rays, electron rays, black-andwhite for high resolving power, ordinary color, X-rays color printing, color diffusion transfer and the like.

Particularly, in case of applying the compounds of the present invention to light-sensitive silver halide color photography, said compounds are usable in combination with 2-equivalent or 4-equivalent couplers. Usable yellow couplers in the present invention include open chain ketomethylene compounds, for example, yellow couplers of pivaloylacetanilide or benzoylacetanilide type.

Usable as magenta couplers in the present invention are compounds of pyrazolone, pyrazolotriazole, pyrazolinobenzimidazole or indazolone type.

Usable colored magenta couplers as masking couplers generally include such compounds as having substituted an arylazo group at an active point of colorless magenta couplers.

Further, there can also be used colored magenta couplers of such type that dyes flow into processing solutions as a result of reaction of the coupler with an oxidation product of a color developing agent at the time of color development.

Cyan couplers usable in the present invention are generally phenol or naphthol derivatives.

Colored cyan couplers usable as masking couplers generally include such compounds as having substituted an arylazo group at an active point of colorless cyan couplers. Further, there can also be used colored cyan couplers of such type that dyes flow into processing solutions on reaction of the coupler with an oxidation product of a color developing agent at the time of color development.

Furthermore, the light-sensitive silver halide photographic materials of the present invention may also contain such couplers called competing couplers as capable of forming colorless dyes.

Silver halide photographic emulsions used in the present invention may be prepared according to a variety of procedures, wherein the silver halide is dispersed into a hydrophilic high molecular substance, such as gelatin, so as to form colloidal particles thereof in the resulting dispersion, said silver halide being silver chloride, silver bromide, silver chlorobromide, silver chloroiodide, silver iodobromide or silver chloroiodobromide.

This silver emulsion may contain various additives commonly used in ordinary silver halide photographic emulsions, for example, various known chemical sensitizers, stabilizers, antifoggants, film hardeners, photosensitive dyes, surface active agents, etc.

The light-sensitive silver halide photographic material containing the compound of the present invention basically comprises a support and thereon a photosensitive layer or layers. According to the purpose of a light-sensitive silver halide photographic material, however, other layer, such as a sub layer, intermediate layer, filter layer, curl preventing layer, protective layer or the like, may additionally be formed on the support either singly or in appropriate combination. Furthermore, the photosensitive layer, per se, may be composed of a double layer comprising two emulsions, one of which is high in sensitivity while the other of which is relatively low in sensitivity, for example, in the same or different wavelength region. The above-mentioned layers may individually contain various photographic additives, for example, those which may be added to the emulsions as aforesaid. Furthermore, according to the object, each of the aforesaid layers may contain a specific additive or additives, for example, a filter layer can contain a dye for filter and a protective layer can contain an agent for improving physical properties of film, antistatic agent or the like.

Still further, the compound of the present invention can be incorporated into any constitutive layers in a light-sensitive silver halide emulsion layer according to the purpose for which said compound is used, for example, the compound can be contained in a single layer such as an emulsion layer, intermediate layer or protective layer, or alternatively can be incorporated into two or more layers, respectively.

Particularly, when the present compound is applied to a multilayer light-sensitive silver halide color photographic material, said compound may be incorporated, according to the purpose for which the compound is used, into any of a blue-sensitive emulsion layer, green-sensitive emulsion layer and red-sensitive emulsion layer, or any of layers respectively adjacent to said emulsion layers. In case where the image effects of the present invention are expected to be obtained, the present compound is preferably incorporated into each of the above-mentioned three emulsion layers or each of the layers respectively adjacent to said three emulsion layers.

Furthermore, the present compounds may be used in combination with the prior art DIR substances, per se, known. In case where undesirable influence is exerted upon photographic characteristics, such as fall in sensitivity, formation of stain or degradation of emulsions in storability by the incorporation into the emulsion layers of DIR substances beyond the scope of the present invention, the addition of such DIR substances is scarcely needed.

In practicing the incorporation into a light-sensitive silver halide photographic material of the compounds of the present invention, said compounds may be contained in a variety of forms in coating liquids for forming constitutive layers of the photographic material. In that case, various techniques heretofore adopted for the incorporation of photographic couplers are applicable just as they are.

The amount of the present compound to be used is 0.1 to 50 g, desirably 1 to 10 g, per 1 kg of an emulsion, though said amount may vary depending on the type of photographic materials to which said compound is applied, the object for which said compound is used, or the effect expected by the use of said compound. When the present compound is used in the same amount as in the prior art DIR substance, the image effects obtained thereby are markedly prominent and, on the other hand, the compound may be used in a very small amount when substantially the same image effects as in the prior art DIR substance are expected.

Light-sensitive silver halide photographic materials containing the compounds of the present invention are preferably developed after exposure with developers comprising, as color developing agents, aromatic primary amine compounds, particularly p-phenylenediamine type compounds. The p-phenylenediamine type compounds include, for example, 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, 3-methyl-4-amino-N-ethyl-N-$\beta$-methoxyethylaniline, 3-$\beta$-methanesulfonamidoethyl-4-amino-N,N-diethylaniline, 3-methoxy-4-amino-N-ethyl-N-$\beta$-hydroxyethylaniline, 3-methoxy-4-amino-N-ethyl-N-β-methoxyethylaniline, 3-acetamido-4-amino-N,N-diethylaniline, 4-amino-N,N-dimethylaniline, N-ethyl-N-β-[β-(β-methoxyethoxy)ethoxy ethyl-3-methyl-4-aminoaniline, N-ethyl-N-β-(β-methoxyethoxy)ethyl-3-methyl-4-aminoaniline or salts thereof, for example, sulfates, hydrochlorides, sulfites and p-toluenesulfonates. Further, such compounds also usable as color developing agents are those disclosed, for example, in Japanese Laid-Open-to-Public Publications Nos. 64932/1973, 131526/1975 and 95849/1976 and Bent et al., Journal of American Chemical Society, 73, 100–3125 (1951).

The color developer solution may be incorporated, if necessary, with various additives, for example, an alkali agent, pH regulator, buffer, development accelerator, antifoggant, preservative, etc.

The light-sensitive silver halide photographic material which has been developed according to the procedure mentioned above may be subjected thereafter to ordinary photographic treatment including the steps of stopping, stop-fixing, fixing, bleaching, bleach-fixing, stabilizing, water washing and drying, and these steps may be suitably combined together according to the type of the light-sensitive photographic material to be processed thereby.

The present invention is illustrated more fully hereinafter with reference to examples, but is should be construed that embodiments of the invention are not limited only to these examples.

EXAMPLE 1

Sample-I, II, III, IV and V were prepared in the following manner.

Sample-I

A solution of 1.0 g of exemplified compound (2) and 15 g of a magenta coupler, 1-(2,4,6-trichlorophenyl)-3-[3-(2,4-di-t-amylphenoxyacetamido)benzamido]-5-pyrazolone in a mixture of 30 ml of ethyl acetate and 15 ml of dibutyl phthalate was mixed with 20 ml of a 10% aqueous solution of Alkanol B (produced and sold by Du Pont Co.) and 200 ml of a 5% aqueous gelatin solution, and the resulting mixture was emulsified by means of a colloid mill to prepare a dispersion. Thereafter, this dispersion was incorporated into 1 kg of a green-sensitive silver iodobromide emulsion (containing 3.0 mol% of silver iodide) to prepare a homogeneous dispersion which was then coated on a cellulose triacetate film base and then dried.

Sample-II

The same procedure as in the case of the sample-I was repeated, except that exemplified compound (17) was used in place of the exemplified compound (2) used in the sample-I, to prepare the sample-II.

Sample-III

* The same procedure as in the case of the sample-I was repeated, except that exemplified compound (20) was used in place of the exemplified compound (2) used in the sample-I, to prepare the sample-III.

Sample-IV

The same procedure as in the case of the sample-I was repeated, except that comparative compound (A) was used in place of the sample-I used in the sample-I, to prepare the sample-IV.

Comparative compound (A)

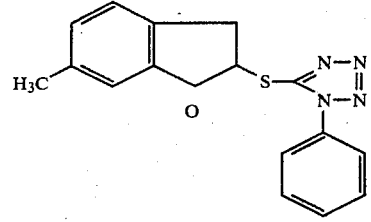

Sample-V

The sample procedure as in the case of the sample-I was repeated but without using the exemplified compound (2) of the sample-I, to prepare the sample-V as a control sample.

After wedgewise exposure to light, the thus prepared sample-I, II, III, IV and V were individually processed according to the following processing steps.

| Processing step (38° C.) | Processing time |
|---|---|
| Color developing | 3 minutes 15 seconds |
| Bleaching | 6 minutes 30 seconds |
| Water washing | 3 minutes 15 seconds |
| Fixing | 6 minutes 30 seconds |
| Water washing | 3 minutes 15 seconds |
| Stabilization bath | 1 minute 30 seconds |

Each of the processing solutions used in the above-mentioned processing steps had the following composition.

| (Composition of color developer) | |
|---|---|
| 4-Amino-3-methyl-N-ethyl-N-(β-hydroxyethyl)aniline sulfate | 4.75 g |
| Anhydrous sodium sulfite | 4.25 g |
| Hydroxylamine ½ sulfate | 2.0 g |
| Anhydrous potassium carbonate | 37.5 g |
| Sodium bromide | 1.3 g |
| Nitrilotriacetic acid trisodium salt (monohydrate) | 2.5 g |
| Potassium hydroxide | 1.0 g |
| Water to make 1 liter and adjust to pH 10.0 with potassium hydroxide. | |
| (Composition of bleaching solution) | |
| Iron ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| Water to make 1 liter and adjust to pH 6.0 with ammonia water. | |
| (Composition of fixing solution) | |
| Ammonium thiosulfate (50% aqueous solution) | 162 ml |
| Anhydrous sodium sulfite | 12.4 g |
| Water to make 1 liter and adjust to pH 6.5 with acetic acid. | |
| (Composition of stabilizing solution) | |
| Formalin (37% aqueous solution) | 5.0 ml |
| Konidax (produced and sold by Konishiroku Photo Industry Co., Ltd.) | 7.5 ml |
| Water to make | 1 liter |

The samples thus processed were individually measured in speed, fog, gamma and DIR effect to obtain the results as shown in Table 1.

TABLE 1

| Sample | Chromogenic characteristics | | | DIR effect |
|---|---|---|---|---|
| | Speed | Fog | Gamma | |
| I | 97 | 0.08 | 0.59 | 41 |

TABLE 1-continued

| Sample | Chromogenic characteristics | | | DIR effect |
|---|---|---|---|---|
| | Speed | Fog | Gamma | |
| II | 98 | 0.09 | 0.54 | 45 |
| III | 95 | 0.08 | 0.55 | 44 |
| IV | 93 | 0.10 | 0.70 | 35 |
| V | 100 | 0.23 | 1.05 | 0 |

As shown in Table 1 above, it is understood that the sample-I, II and III according to the present invention, as compared with the sample-IV, demonstrate a large drop in gamma value and are excellent in DIR effect. Further, the magenta images obtained on the samples of the present invention were found to be fine in graininess. In the above table, the speed was represented by a relative value as measured by assuming as 100 the speed of the sample-V, and the gamma was represented by tan θ of the straight line portion of the characteristic curve. The DIR effect was represented by a numerical value calculated on the basis of an equation $(1-D_T) \times 100$, and the larger is the numerical value, the larger is the DIR effect. In the above equation, $D_T$ represents a density of each of the sample-I, II, III and IV as measured at the same exposure amount as in the case of the sample-V while density as measured being 1.0.

EXAMPLE 2

The samples used in Example 1 were individually stored for 3 days under 60% humidity conditions (DT) and separately were individually stored for 14 days under 80% humidity conditions (HT). Thereafter, the samples were individually subjected to color development treatment in the same manner as in Example 1 to determine their stability. The results obtained were as shown in Table 2.

TABLE 2

| | Speed | | | Gamma | | | Maximum density | | |
|---|---|---|---|---|---|---|---|---|---|
| Sample | Not treated | DT | HT | Not treated | DT | HT | Not treated | DT | HT |
| I | 97 | 96 | 93 | 0.58 | 0.57 | 0.55 | 1.2 | 1.2 | 1.1 |
| II | 97 | 97 | 95 | 0.56 | 0.55 | 0.53 | 1.1 | 1.1 | 1.0 |
| III | 96 | 95 | 92 | 0.56 | 0.54 | 053 | 1.1 | 1.1 | 1.0 |
| IV | 91 | 84 | 77 | 0.63 | 0.58 | 0.50 | 1.3 | 1.1 | 0.9 |
| V | 100 | 98 | 96 | 1.02 | 100° | 0.94 | 2.3 | 2.2 | 2.2 |

As is clear from the above table, it is understood that the sample-I, II and III of the present invention, as compared with the sample-IV, are very stable and are found to be useful as DIR substances.

EXAMPLE 3

Sample-VI, VII and VIII were prepared in the following manner.

Sample-VI

A solution of 1.0 g of exemplified compound (3) and 10 g of a cyan coupler 1-hydroxy-2-N-[δ-(2,4-di-tert-amylphenoxy)butyl]naphthamide in a mixture of 20 ml of ethyl acetate and 10 ml of dibutyl phthalate was mixed with 20 ml of a 10% aqueous solution of Alkanol B (produced and sold by Du Pont Co.) and 200 ml of a 5% aqueous gelatin solution, and the resulting mixture was emulsified by a colloid mill to prepare a dispersion. Thereafter, this dispersion was incorporated into 1 kg of a red-sensitive silver iodobromide emulsion (containing 3.0 mol% of silver iodide) to prepare a homogeneous dispersion. The dispersion was then coated on a cellulose triacetate base and dried to prepare the sample-VI.

Sample-VII

The sample-VII as a comparative sample was prepared in exactly the same manner as in the case of the sample-VI, except that comparative compound (B) of the following formula was used in place of the exemplified compound (3) used in the sample-VI.

Comparative compound (B)

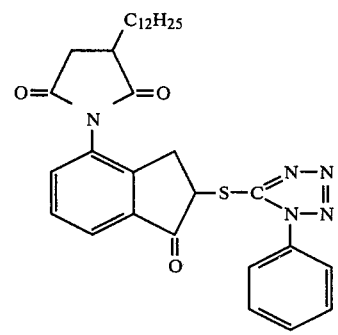

Sample-VIII

As a control sample, there was prepared the sample-VIII in exactly the same manner as in the case of the sample-VI but without using the exemplified compound (3) which had been used in the sample-VI.

After wedgewise exposure, the thus prepared sample-VI, VII and VIII were individually processed according to the same processing step as in Example 1 and measured in speed, gamma, maximum density and DIR effect to obtain the results as shown in Table 3.

TABLE 3

| | Speed | | | Gamma | | | Maximum density | | | DIR effect |
|---|---|---|---|---|---|---|---|---|---|---|
| Sample | Not treated | DT | HT | Not treated | DT | HT | Not treated | DT | HT | |
| VI | 98 | 94 | 92 | 0.52 | 0.50 | 0.49 | 0.80 | 0.75 | 0.72 | 44 |
| VII | 93 | 88 | 83 | 0.60 | 0.57 | 0.51 | 0.87 | 0.79 | 0.70 | 35 |
| VIII | 100 | 98 | 97 | 0.85 | 0.84 | 0.83 | 1.63 | 1.60 | 1.57 | 0 |

As is the case with Example 1, the cyan dye image obtained on the sample-VI, as compared with those obtained on the sample-VII and VIII, demonstrated a large drop in gamma value and was excellent in DIR effect, and further the cyan image formed on the sample-VI was found to favorably fine in graininess.

Similarly, samples prepared in the same manner as above but using respectively exemplified compounds (8), (11), (17) and (20), respectively, in place of the exemplified compound (3) used in the sample-VI, demonstrated also favorable results similar to those of this example.

Further, a sample was prepared in the same manner as in the case of the sample-VI, except that the exemplified compound (3) and the cyan coupler were individually dissolved in ethyl acetate and dibutyl phthalate, respectively, and thereafter, individually emulsified by means of a colloid mill to prepare their respective dispersions, the coupler dispersion was incorporated into the red-sensitive silver iodobromide emulsion, followed by incorporating thereinto the DIR dispersion containing the exemplified compound (3), and the resulting emulsion was coated on the cellulose triacetate base and then dried. The sample thus prepared was processed and measured in the same manner as in this example to demonstrate the same results as in the sample-VI.

EXAMPLE 4

Sample-IX was prepared in exactly the same manner as in the case of the sample-VI of Example 3, except that exemplified compound (15) was used in place of the exemplified compound (3) used in the sample-VI.

Separately, comparative sample-X was prepared in exactly the same manner as in the case of the sample-VI of Example 3, except that comparative compound of the following formula was used in place of the exemplified compound (3).

Comparative compound (C)

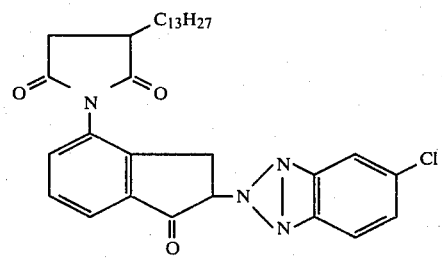

These samples as prepared above were subjected, after wedgewise exposure, to the same processing step as in Example 1 and then measured in photographic characteristics. As the result, the sample-IX demonstrated favorable results that as compared with the comparative sample-X, the sample-IX of the present invention demonstrates large drop in gamma value and is excellent in DIR effect, and further than the cyan image obtained on the sample-IX is found to be fine in graininess.

EXAMPLE 5

Sample-XI, a high speed multilayer light-sensitive color negative photographic material, was prepared by successively coating the following layers on the surface of a transparent cellulose triacetate base support which had been subjected to subbing treatment.

First layer: Antihalation layer
 A gelatin solution containing black colloid silver was coated in the proportion of 0.3 g/m² of silver.
 (Dry film thickness: 3μ)
Second layer: Intermediate layer
 An aqueous gelatin solution was coated.
 (Dry film thickness: 1μ)

Third layer: A red-sensitive low speed silver halide emulsion layer
 After chemical sensitization with a gold sensitizer and sulfur sensitizer, a silver iodobromide emulsion containing 4 mol% of silver iodide (average particle diameter: 0.4μ) was subjected to color sensitization with addition of 0.25 g of D-(1) and 0.06 g of D-(2) as red-sensitivity sensitizing dyes, which will be explained later, per mole of silver halide, and was then incorporated with 1 g of 4-hydroxy-6-methyl-1,3,3a,7-tetrazaindene and 40 mg of 1-phenyl-5-mercaptotetrazole and further with a cyan coupler dispersion-1 which will be explained later. The red-sensitive low speed silver halide emulsion thus obtained was coated in the proportion of 18 g/m² of silver.
 (Dry film thickness: 3.8μ)
Fourth layer: A red-sensitive high speed silver halide emulsion layer
 After chemical sensitization with a gold sensitizer and sulfur sensitizer, a silver iodobromide emulsion (average particle diameter: 1.2μ) containing 7 mol% of silver iodide was subjected color sensitization with addition of 0.13 g of D-(1) and 0.03 g of D-(2) as red-sensitivity sensitizing dyes, which will be explained later, per mole of silver halide, and was then incorporated with 1 g of 4-hydroxy-6-methyl-1,3,3a,7-tetrazaindene and 12 mg of 1-phenyl-5-mercaptotetrazole and further with a cyan coupler dispersion-2 which will be explained later. The red-sensitive high speed silver halide emulsion was coated in the proportion of 10 g/m² of silver.
 (Dry film thickness: 2μ)
Fifth layer: An intermediate layer
 This layer was the same as the second layer.
Sixth layer: A green-sensitive low speed silver halide emulsion layer
 After chemical sensitization with a gold sensitizer and sulfur sensitizer, a silver iodobromide emulsion containing 5 mol% of silver iodide (average particle diameter: 0.8μ) was subjected to color sensitization with addition of 0.11 g of D-(3), 0.08 g of D-(4) and 0.09 g of D-(5) as green-sensitivity sensitizers, which will be explained later, per mole of silver halide, and was then incorporated with 1 g of 4-hydroxy-6-methyl-1,3,3a,7-tetrazaindene and 40 mg of 1-phenyl-5-mercaptotetrazole and further with a magenta coupler dispersion-1 which will be explained later.
 The green-sensitive low speed silver halide emulsion thus obtained was coated in the proportion of 14 g/m² of silver.
 (Dry film thickness: 4μ)
Seventh layer: A green-sensitive high speed silver halide emulsion layer
 After chemical sensitization with a gold sensitizer and sulfur sensitizer, a silver iodobromide emulsion (average particle diameter: 1.2μ) containing 7 mol% of silver iodide was subjected to color sensitization with addition of 0.09 g of D-(3), 0.07 g of D-(4) and 0.08 g of D-(5) as green-sensitivity sensitizing dyes, which will be explained later, per mole of silver halide, and was then incorporated with 1 g of 4-hydroxy-6-methyl-1,3,3a,7-tetrazaindene and 10 mg of 1-phenyl-5-mercaptotetrazole and further with a magenta coupler dispersion-2 which will be explained later.

The green-sensitive high speed silver halide emulsion thus obtained was coated in the proportion of 12 g/m² of silver.
(Dry film thickness: 1.8μ)

Eighth layer: An intermediate layer
This layer was the same as the second layer.

Ninth layer: A yellow filter layer
An aqueous gelatin solution containing yellow colloid silver and a dispersion of 2,5-di-t-octylhydroquinone was coated in the proportion of 0.1 g/m² of silver.

Tenth layer: A blue-sensitive low speed silver halide emulsion layer
After chemical sensitization with a gold sensitizer and sulfur sensitizer, a silver iodobromide emulsion (average particle diameter: 0.6μ) containing 8 mol% of silver iodide was incorporated with 1 g of 4-hydroxy-6-methyl-1,3,3a,7-tetrazaindene, 80 mg of 1-phenyl-5-mercaptotetrazole and 2 g of 1,2-bisvinylsulfonylethane and further with a yellow coupler dispersion. The blue-sensitive low speed silver halide emulsion thus prepared was coated in the proportion of 5 g/m² of silver.

Eleventh layer: A blue-sensitive high speed silver halide emulsion layer
After chemical sensitization with a gold sensitizer and sulfur sensitizer, a silver iodobromide emulsion (average particle diameter: 1.2μ) containing 7 mol% of silver iodide was incorporated with 60 mg of 4-hydroxy-6-methyl-1,3,3a,7-tetrazaindene and 2 g of 1,2-bisvinylsulfonylethane and further with a yellow coupler dispersion which will be explained later.
The blue-sensitive high speed silver halide emulsion thus prepared was coated in the proportion of 7 g/m² of silver.
(Dry film thickness: 3μ)

Twelfth layer: A protective layer
An aqueous gelatin solution containing 1,2-bisvinylsulfonylethane was coated.
(Dry film thickness: 1.2μ)

The coupler dispersions used in the third, fourth, sixth, seventh, tenth and eleventh layers respectively were prepared in the following manner.

Cyan coupler dispersion-1

In a mixture of 22 g of tricresyl phosphate and 140 g of ethyl acetate were dissolved 39 g of 1-hydroxy-N-[δ-(2,4-di-t-amylphenoxy)butyl]-2-naphthamide as a cyan coupler, 2 g of 1-hydroxy-4-[4-(1-hydroxy-8-acetamido-3,6-disulfo-2-naphthylazo)phenoxy]-N-[δ-(2,4-di-t-amylphenoxy)butyl]-2-naphthamide disodium salt as a colored coupler and 2.5 g of exemplified compound (3) as a DIR substance. The resulting solution was incorporated into 450 ml of a 7.5% aqueous gelatin solution containing 1.5 g of Alkanol B (produced and sold by Du Pont Co.), and the resulting mixture was emulsified by means of a colloid mill to prepare the title dispersion.

Cyan coupler dispersion-2

In a mixture of 18 g of tricresyl phosphate and 110 g of ethyl acetate were dissolved 30 g of 1-hydroxy-4-isopropylaminocarbonylmethoxy-N-dodecyl-2-naphthamide as a cyan coupler, 2 g of the same colored coupler as that used in the cyan coupler dispersion-1, 4.0 g of exemplified compound (3) as a DIR substance and 0.5 g of laurylester of gallic acid. The resulting solution was incorporated into 350 ml of a 7.5% aqueous gelatin solution containing 1.4 g of Alkanol B (produced and sold by Du Pont Co.), and the resulting mixture was emulsified by means of a colloid mill to prepare the title dispersion.

Magenta coupler dispersion-1

In a mixture of 60 g of tricresyl phosphate and 180 g of ethyl acetate were dissolved 50 g of 1-(2,4,6-trichlorophenyl)-3-[3-(2,4-di-t-amylphenoxyacetamido)-benzamido]-5-pyrazolone as a magenta coupler, 10 g of 1-(2,4,6-trichlorophenyl)-4-(1-octylazo)-3-(2-chloro-5-octadecenylsuccinimidoanilino)-5-pyrazolone as a colored coupler and 1.5 g of exemplified compound (3) as a DIR substance. The resulting solution was incorporated into 670 ml of a 7.5% aqueous gelatin solution containing 2 g of Alkanol B, and the resulting mixture was emulsified by means of a colloid mill to prepare the title dispersion.

Magenta coupler dispersion-2

In a mixture of 14 g of diethyl laurylamine, 14 g of tricresyl phosphate and 45 g of ethyl acetate were dissolved 10 g 4,4'-methylenebis-[1-(2,4,6-trichlorophenyl)3-{3-(2,4,6-di-t-amylphenoxyacetamido}-5-pyrazolone] as a magenta coupler, 2.9 g of the same colored coupler as that used in the magenta coupler dispersion-1 and 1 g of exemplified compound (3) as a DIR substance. The resulting solution was incorporated into 200 ml of a 7.5% aqueous gelatin solution containing 2.5 g of Alkanol B, and the resulting mixture was emulsified by means of a colloid mill to prepare the title dispersion.

Yellow coupler dispersion

In a mixture of 100 g of dibutyl phosphate and 560 g of ethyl acetate was dissolved 200 g of α-(1-benzyl-2-phenyl-3,5-dioxo-1,2,4-triazolidine-4-yl)-α-pivaloyl-2-chloro-5-[γ-(2,4-di-t-amylphenoxy)butylamido]acetanilide, and the resulting solution was incorporated into 1500 ml of a 7.5% aqueous gelatin solution containing 22 g of Alkanol B. The resulting mixture was emulsified by means of a colloid mill to prepare the title dispersion. The aforesaid color sensitizing dyes D-(1), D-(2), D-(3), D-(4) and D-(5) used in the aforesaid photographic emulsion layers had their respective structures as mentioned below.

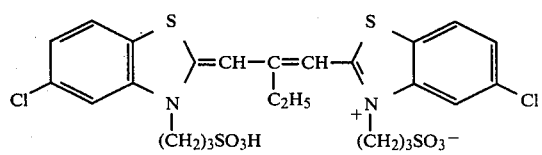

D-1

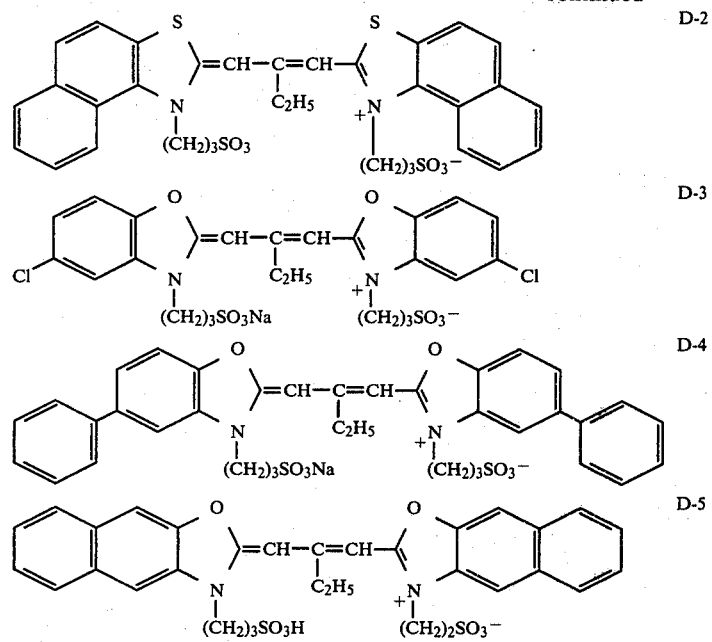

Further, sample-XII was prepared in the same manner as in the case of the sample-XI, except that the comparative compound (B) of Example 3 was used in the third and sixth layers respectively in place of the exemplified compound (3) used in said layers respectively in the sample-XI.

The samples thus prepared were individually subjected to separation exposure through blue, green and red filters respectively and then subjected to color development in the same manner as in Example 1. The color images obtained were measured in photographic characteristics to obtain the results as shown in Table 4.

TABLE 4

| Sample | Speed Not treated | | | Speed HT | | | Inter image effect | | | Graininess (RMS) | |
|---|---|---|---|---|---|---|---|---|---|---|---|
| | Y | M | C | Y | M | C | Y | M | C | M | C |
| XI | 100 | 100 | 100 | 98 | 94 | 97 | 1.07 | 1.52 | 1.46 | 40 | 38 |
| XII | 97 | 95 | 97 | 94 | 89 | 95 | 1.05 | 1.50 | 1.44 | 41 | 39 |

As is clear from the above table, the samples-XI and XII according to the present invention are excellent in stability and also favorable in graininess.

In Table 4 above, the graininess (RMS) was represented by a value 1000 time the standard deviation of variations in density value brought about when the image was subjected to scanning by means of a microdensitometer of 25μ in circular scanning caliber, and the inter image effect was represented by the undermentioned value based on analytical gamma obtained by measuring an analytical density of each color image forming unit layer. The larger is the under-mentioned value, the larger is the inter image effect.

Inter image effect:

$$\text{Inter image effect on yellow image forming unit layer} = \frac{\text{Analytical gamma of yellow image forming unit layer exposed to blue light}}{\text{Analytical gamma of yellow image forming unit layer exposed to white light}}$$

$$\text{Inter image effect on magenta image forming unit layer} = \frac{\text{Analytical gamma of magenta image forming unit layer exposed to green light}}{\text{Analytical gamma of magenta image forming unit layer exposed to white light}}$$

$$\text{Inter image effect on cyan image forming unit layer} = \frac{\text{Analytical gamma of cyan image forming unit layer exposed to red light}}{\text{Analytical gamma of cyan image forming unit layer exposed to white light}}$$

EXAMPLE 6

Sample-XIII was prepared in the same manner as in the case of the sample-XI of example 5, except that the under-mentioned cyan coupler and magenta coupler were used in the fourth and seventh layers respectively in place of the cyan coupler dispersion-2 and magenta coupler dispersion-2 used in said layers respectively in the sample-XI.

Sample-XIV was prepared in the same manner as in the case of sample-XIII, except that the comparative DIR substance (B) was used in the third, fourth and sixth layers respectively in place of the exemplified compound (3) used in said layers respectively in the sample-XI.

Cyan coupler dispersion

In a mixture of 25 g of tricresyl phosphate and 150 g of ethyl acetate were dissolved 45 g of 1-hydroxy-N-[δ-(2,4-di-t-amylphenoxy)butyl)]-2-naphthamide as a cyan coupler, 2 g of 1-hydroxy-4-[4-(1-hydroxy-8-acetamido-3,6-disulfo-2-naphthylazo)phenoxy]-N-[δ-(2,4-di-t-amylphenoxy)butyl]-2-naphthamide disodium salt and 2.5 g of exemplified compound (3) and 0.5 g of lauryl ester of gallic acid as DIR substances, and the resulting solution was incorporated into 480 ml of a 7.5% aqueous gelatin solution containing 1.7 g of Alkanol B. The resulting mixture was emulsified by means of a colloid mill to prepare the title dispersion.

Magenta coupler dispersion

In a mixture of 20 g of tricresyl phosphate and 45 g of ethyl acetate were dissolved 10 g of 1-(2,4,6-trichlorophenyl)-3-[3-(2,4-di-t-amylphenoxyacetamido)benzamido]-5-pyrazolone as a magenta coupler, 2.9 g of 1-(2,4,6-trichlorophenyl)-4-(4-methoxyphenylazo-3-[3-(2,4-di-t-amylphenoxyacetamido)benzamido]-5-pyrazolone as a colored coupler and 1 g of 2,4-di-t-octylhydroquinone. The resulting solution was incorporated into 170 ml of a 7.5% aqueous gelatin solution containing 2 g of Alkanol B, and the resulting mixture was emulsified by means of a colloid mill to prepare the title dispersion.

The samples thus prepared were individually subjected to color development treatment in the same manner as in Example 5. Photographic characteristics of each of the images obtained were found to be favorably similar to those obtained in Example 5.

What we claim is:

1. A photographic material comprising a light-sensitive silver halide emulsion layer coated on a support, which material is characterized by containing a compound represented by the following general formula [I]:

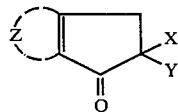

General formula [I]

wherein X represents hydrogen or halogen atom, Y represents a group capable of being released, when said compound of the general formula reacts with an oxidation product of a color developing agent, and of forming an arylmercapto compound, a heterocyclic mercapto compound or a triazole compound which has no mercapto group, each having a development inhibiting action, and Z represents a nonmetal atomic group necessary for forming a benzene ring, said benzene ring having been substituted by at least one —S—R group and/or a group having at least one —S—R group in which R represents an alkyl, aryl or heterocyclic group.

2. A photographic material according to claim 1 in which Y represents a mercapto tetrazol or triazole-residue.

3. A photographic material according to claim 2 in which Y represents a 1-phenyl-5-mercapto tetrazole or benzotriazole residue.

4. A photographic material comprising a light-sensitive silver halide emulsion layer coated on a support, which material is characterized by containing a compound represented by the following formula [Ib]:

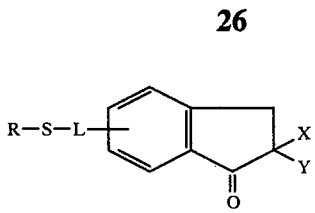

Formula (Ib)

wherein X represents hydrogen or halogen atom, Y represents a group capable of being released, when said compound of the general formula reacts with an oxidation product of a color developing agent, and of forming an arylmercapto compound, a heterocyclic mercapto compound or a triazole type compound which has no mercapto group, each having a development inhibiting action, L represents a connecting group and R represents an alkyl, aryl or 5- or 6-membered heterocyclic ring containing a nitrogen, oxygen and/or sulfur atom.

5. A photographic material according to claim 4 in which L represents a 5- or 6-membered heterocyclic residue containing a nitrogen or oxygen atom or aryl group residue.

6. A photographic material according to claim 4 in which the compound is represented by the following formulae:

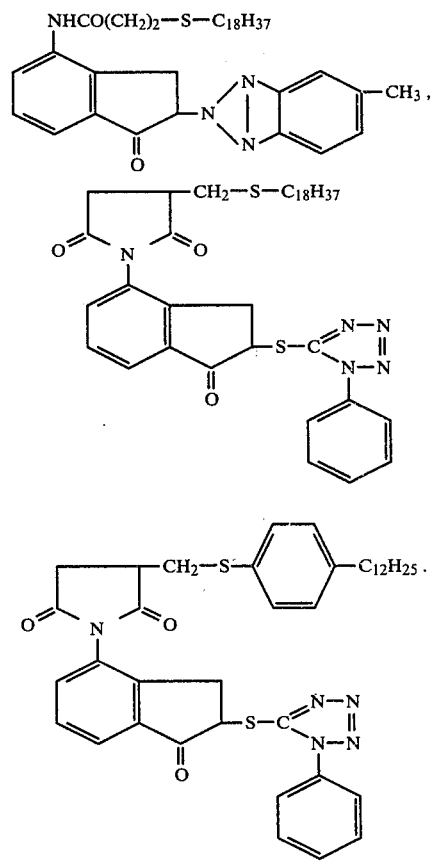

7. A photographic material according to claim 1 in which the heterocyclic group of R is a 5- or 6-membered heterocyclic ring containing a nitrogen, oxygen and/or sulfur atom.

* * * * *